United States Patent
Morrissey et al.

(10) Patent No.: US 8,454,822 B2
(45) Date of Patent: Jun. 4, 2013

(54) DISPOSABLE TANGENTIAL FLOW FILTRATION LINER WITH SENSOR MOUNT

(75) Inventors: Martin Morrissey, Billerica, MA (US); Dennis Wong, Billerica, MA (US)

(73) Assignee: EMD Millipore Corporation, Billerica, MA (US)

( * ) Notice: Subject to any disclaimer, the term of this patent is extended or adjusted under 35 U.S.C. 154(b) by 312 days.

(21) Appl. No.: 12/784,094

(22) Filed: May 20, 2010

(65) Prior Publication Data

US 2011/0127203 A1     Jun. 2, 2011

Related U.S. Application Data

(60) Provisional application No. 61/217,323, filed on May 29, 2009.

(51) Int. Cl.
*B01D 35/14* (2006.01)
*B01D 65/00* (2006.01)
*G01L 7/08* (2006.01)

(52) U.S. Cl.
USPC ............... 210/90; 73/715; 73/866.5; 96/421; 210/85; 210/321.84; 210/498

(58) Field of Classification Search
USPC ............ 210/85, 90, 103, 232, 321.6, 321.75, 210/321.84, 455, 484, 488, 498; 96/9, 11, 96/417, 421; 73/866.5, 861.47, 715–728
See application file for complete search history.

(56) References Cited

U.S. PATENT DOCUMENTS

| | | |
|---|---|---|
| 3,085,970 A | 4/1963 | Davis |
| 3,520,803 A | 7/1970 | Iaconelli |
| 4,261,834 A | 4/1981 | deWinter |
| 4,556,489 A | 12/1985 | Diettrich, Jr. et al. |
| 4,732,675 A | 3/1988 | Badolato et al. |
| 4,849,102 A | 7/1989 | Latour et al. |
| 4,867,876 A | 9/1989 | Kopf |
| 4,902,481 A | 2/1990 | Clark et al. |
| 5,034,124 A | 7/1991 | Kopf |
| 5,049,268 A | 9/1991 | Kopf |
| 5,096,582 A | 3/1992 | Lombardi et al. |

(Continued)

FOREIGN PATENT DOCUMENTS

| | | |
|---|---|---|
| CN | 2064262 U | 10/1990 |
| CN | 1210476 A | 3/1999 |

(Continued)

OTHER PUBLICATIONS

European communication dated Dec. 20, 2010 in co-pending foreign application.

(Continued)

*Primary Examiner* — Joseph Drodge

(74) *Attorney, Agent, or Firm* — Nields, Lemack & Frame, LLC

(57) ABSTRACT

Tangential flow filtration device is provided wherein liners are provided between the filtration element and the top and bottom holders or manifolds. The liners incorporate the flow channels and inlet and outlet ports, as well as a sensor mount. The liners are made of an inexpensive material and therefore are disposable after a single use, making it more cost effective to dispose of them than to clean the conventional manifolds. The sensor mount accommodates a removable sensor, and isolates it from the fluid path.

6 Claims, 3 Drawing Sheets

U.S. PATENT DOCUMENTS

| | | | |
|---|---|---|---|
| 5,147,542 | A | 9/1992 | Proulx |
| 5,176,828 | A | 1/1993 | Proulx |
| 5,258,122 | A | 11/1993 | Ha et al. |
| 5,342,517 | A | 8/1994 | Kopf |
| 5,429,742 | A | 7/1995 | Gutman et al. |
| 5,443,723 | A | 8/1995 | Stankowski et al. |
| 5,445,737 | A | 8/1995 | Ondrick |
| 5,599,447 | A | 2/1997 | Pearl et al. |
| 5,693,892 | A * | 12/1997 | Batey .................. 73/861.12 |
| 5,855,778 | A | 1/1999 | Hutchison et al. |
| 5,868,930 | A | 2/1999 | Kopf |
| 6,736,980 | B2 * | 5/2004 | Moscaritolo .................. 210/741 |
| 6,823,718 | B2 * | 11/2004 | Sandford et al. .................. 73/37 |
| 6,852,216 | B2 * | 2/2005 | Moscaritolo et al. ........... 210/85 |
| 7,094,346 | B2 | 8/2006 | Osenar et al. |
| 7,137,390 | B2 * | 11/2006 | Fudge et al. ............. 128/205.12 |
| 7,306,727 | B2 | 12/2007 | Perreault |
| 7,473,404 | B2 | 1/2009 | Chopard et al. |
| 8,177,974 | B2 | 5/2012 | Hunt et al. |
| 2003/0042182 | A1 | 3/2003 | Moscaritolo |
| 2004/0226875 | A1 | 11/2004 | Bartlett et al. |
| 2006/0060518 | A1 * | 3/2006 | Perreault .................. 210/321.6 |
| 2007/0023344 | A1 | 2/2007 | Kemp |
| 2007/0023348 | A1 | 2/2007 | Harms et al. |
| 2007/0138082 | A1 | 6/2007 | Connors, Jr. et al. |
| 2007/0241048 | A1 | 10/2007 | Hunt et al. |
| 2008/0257813 | A1 | 10/2008 | Proulx et al. |
| 2009/0060789 | A1 * | 3/2009 | Aas et al. .................. 422/68.1 |
| 2010/0237013 | A1 * | 9/2010 | Burke et al. .................. 210/637 |
| 2011/0174711 | A1 | 7/2011 | Morrissey et al. |
| 2012/0192958 | A1 | 8/2012 | Hunt et al. |

FOREIGN PATENT DOCUMENTS

| | | |
|---|---|---|
| CN | 101134157 A | 3/2008 |
| EP | 1415698 A1 | 5/2004 |
| EP | 1 637 213 A1 | 3/2006 |
| EP | 1 844 846 A2 | 10/2007 |
| EP | 0 345 209 A2 | 8/2010 |
| JP | 53-103983 A | 9/1978 |
| JP | 55-5684 | 1/1980 |
| JP | 8-89766 A | 4/1996 |
| JP | 2000-510722 A | 8/2000 |
| JP | 2003-502140 A | 1/2003 |
| JP | 2006-88152 | 4/2006 |
| JP | 2008-238167 A | 10/2008 |
| WO | 97/28889 A1 | 8/1997 |
| WO | 97/42410 A1 | 11/1997 |
| WO | 00/78429 A2 | 12/2000 |
| WO | 02/085511 A1 | 10/2002 |
| WO | 2008/107652 A1 | 9/2008 |

OTHER PUBLICATIONS

Notice of Allowance mailed Mar. 13, 2012 in co-pending U.S. Appl. No. 11/404,287.
Extended European Search Report received for co-pending EP Patent Application No. 08153282.2, mailed on Jul. 20, 2009, 5 pages.
Office Action mailed Mar. 25, 2010 in co-pending U.S. Appl. No. 12/075,210.
Final Rejection mailed Nov. 26, 2010 in co-pending U.S. Appl. No. 12/075,210.
Office Action dated Jun. 14, 2011 in co-pending U.S. Appl. No. 11/404,287.
Office Action mailed Aug. 7, 2012 in co-pending U.S. Appl. No. 13/446,103.
Bio Pharmaceuticals—no date; Selection Guide System Data Sheet BP-1070; Filtration. Separation. Solution.
BioProcess International; Apr. 2004; p. 33; "Manufacturing Conjugate Vaccines"; Ian Sellick.
European Search Report dated Jan. 12, 2006.
European Search Report dated Aug. 26, 2008.
Japanese communication dated Oct. 21, 2008.
European communication dated Aug. 26, 2009.
European Search Report dated Aug. 19, 2009.
Chinese communication dated Oct. 30, 2009.
Japanese communication dated May 11, 2010 in co-pending foreign application (JP2007-103871).
Chinese communication dated Jun. 2, 2010 in co-pending foreign application (CN-200710128282.3).
Office Actions in co-pending U.S. Appl. No. 11/404,287 dated Mar. 28, 2008, Aug. 20, 2008, Jan. 22, 2009, Jun. 17, 2009, Dec. 4, 2009 and Mar. 29, 2010.
Office Action dated Sep. 10, 2010 in co-pending U.S. Appl. No. 11/404,287.
Japanese Communication, with English translation, mailed Sep. 13, 2011 in corresponding Japanese patent application No. JP 2010-124907.
Final Rejection mailed Nov. 21, 2011 in co-pending U.S. Appl. No. 11/404,287.
Japanese Communication, with English translation, mailed Oct. 25, 2011 in co-pending Japanese patent application No. JP 2010-175454.
European communication dated Oct. 7, 2010 in corresponding foreign application (EP10164404.5).
Chinese Communication issued Sep. 24, 2012 in corresponding Chinese patent application No. CN 201010197766.5.
Office Action mailed Sep. 5, 2012 in co-pending U.S. Appl. No. 12/844,282.
Final rejection mailed Mar. 7, 1013 in co-pending U.S. Appl. No. 12/844,282.
Chinese Communication mailed Nov. 5, 2012 in co-pending Chinese patent application No. 201010281130.9.
Final Rejection mailed Jan. 14, 2013 in co-pending U.S. Appl. No. 13/446,103.

* cited by examiner

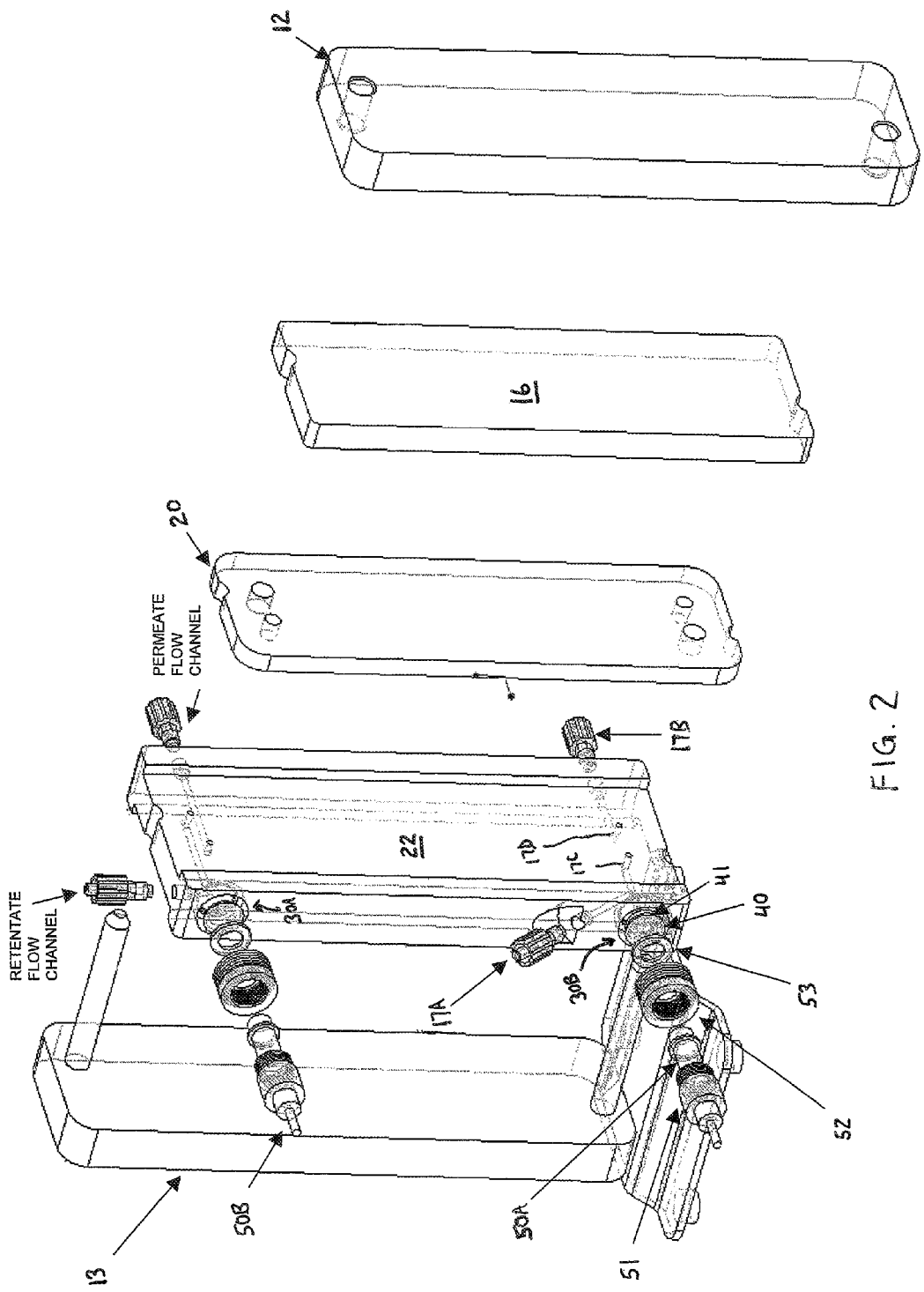

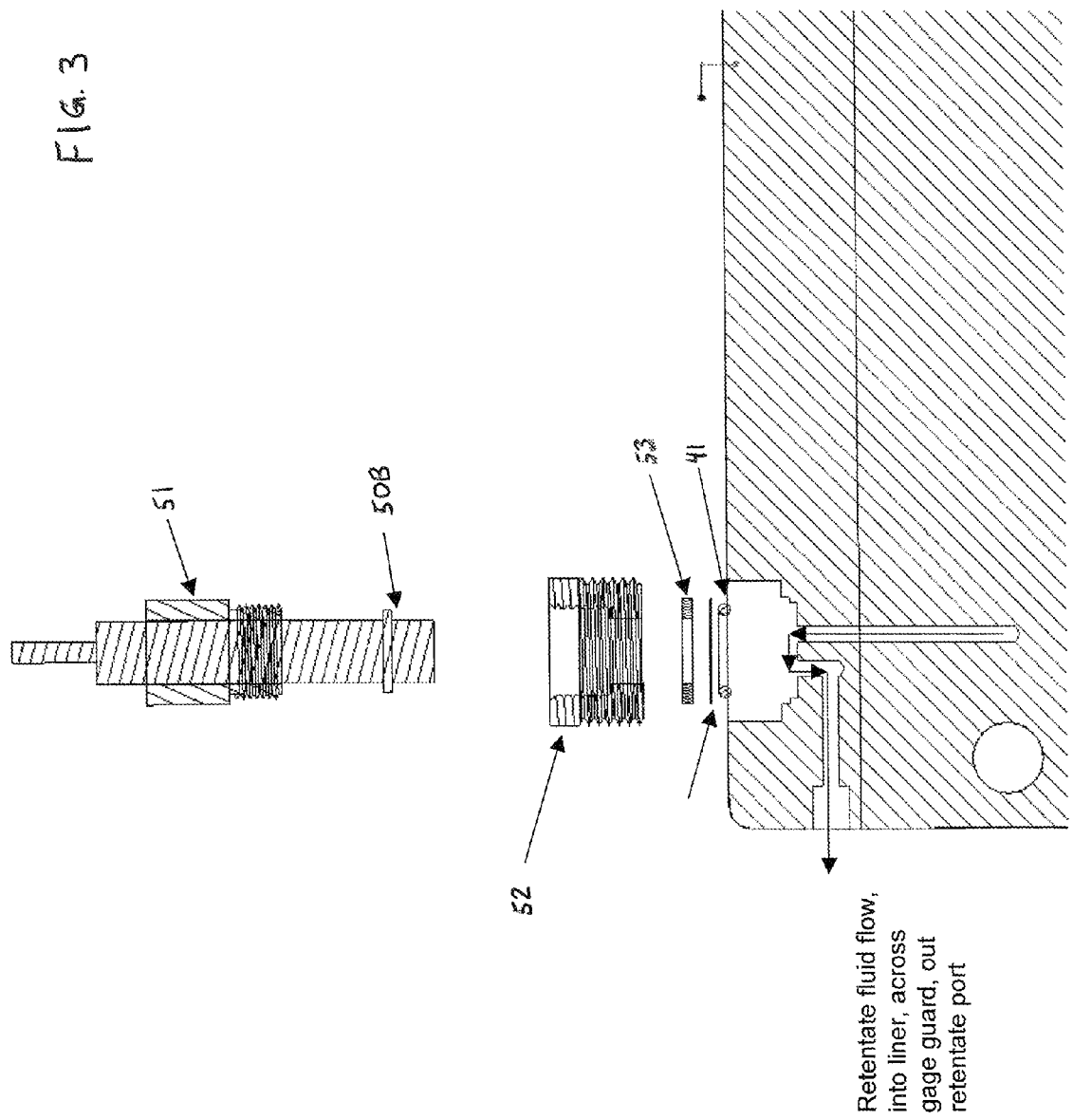

DISPOSABLE TANGENTIAL FLOW FILTRATION LINER WITH SENSOR MOUNT

This application claims priority of U.S. Provisional Application Ser. No. 61/217,323 filed May 29, 2009, the disclosure of which is incorporated herein by reference.

BACKGROUND OF THE INVENTION

Tangential Flow Filtration (TFF) is a separation process that uses membranes to separate components in a liquid solution or suspension on the basis of size or molecule weight differences. Applications include concentration, clarification, and desalting of proteins and other biomolecules such as nucleotides, antigens, and monoclonal antibodies; buffer exchange; process development; membrane selection studies; pre-chromatographic clarification to remove colloidal particles; depyrogenation of small molecules such as dextrose and antibiotics; harvesting, washing or clarification of cell cultures, lysates, colloidal suspensions and viral cultures; and sample preparation.

In TFF, the solution or suspension to be filtered is passed across the surface of the membrane in a cross-flow mode. The driving force for filtration is the transmembrane pressure, usually created with a peristaltic pump in disposable TFF applications. The velocity at which the filtrate is passed across the membrane surface also controls the filtration rate and helps prevent clogging of the membrane. Because TFF recirculates retentate across the membrane surface, membrane fouling is minimized, a high filtration rate is maintained, and product recovery is enhanced.

Conventional TFF devices are formed of a plurality of elements, including a pump, a feed solution reservoir, a filtration module and conduits for connecting these elements. In use, the feed solution is directed from the feed solution reservoir to the filtration module while the retentate from the filtration module is recirculated from the filtration module to the feed solution reservoir until the desired volume of retentate is obtained. The membrane is sandwiched between top and bottom manifolds or holders, which serve to provide accurate mechanical constraint against the internal hydraulic pressure of the device, and also serve to distribute the filtration stream across the multiple flow paths within the device. These manifolds or holders are typically made of stainless steel and must be cleaned and validated prior to each use, particularly in biopharmaceutical and other sanitary applications. This is an expensive and time-consuming process.

Where cleaning and validation steps are desired to be eliminated when replacing the filtration medium, disposable liners can be used instead of the reusable stainless steel liners. The liners incorporate the flow channels and inlet and outlet ports that were previously present in the manifolds, and isolate the process fluid from coming into contact with the TFF holder. The liners can be made of an inexpensive material and therefore are disposable after a single use, making it more cost effective to dispose of them than to clean the conventional manifolds. In addition, the liners can be pre-sterilized. In order to provide sufficient strength and rigidity under operating conditions, the liners can have a grid pattern of ribs that abut the holder plates to help prevent the liners from torquing under clamping force.

It also would be desirable to incorporate sensors in the liners, for measuring various process parameters, such as pressure, without having to clean or sterilize the sensors when replacing the filtration medium and/or liners.

SUMMARY OF THE INVENTION

The shortcomings of the prior art are overcome by the embodiments disclosed herein, which include a tangential filtration assembly including one or more preferably disposable liners having one or more sensors disposed therein. The sensor(s) are isolated from the fluid and are removable from the liner. As a result, after use the liner can be disposed and the sensor(s) reused without having to clean the sensor.

In accordance with certain embodiments, a tangential flow filtration device is provided wherein one or more liners are located between the filtration element and the top and bottom holders or manifolds. The liners incorporate the flow channels and inlet and outlet ports that are conventionally present in the stainless steel manifolds. The liners are made of an inexpensive material and therefore are disposable after a single use, making it more cost effective to dispose of them than to clean the conventional manifolds. In addition, the liners can be pre-sterilized. In order to provide sufficient strength and rigidity under operating conditions, the liners can have a grid pattern of ribs that abut the holder plates to help prevent the liners from torquing under clamping force.

The one or more liners includes one or more sensor ports or mounts, for removably affixing a sensor to the liner. A diaphragm is disposed between the sensor and the fluid passageway in the liner, isolating the sensor components from directly contacting fluid in the passageway. The sensor remains capable of sensing the pressure of the fluid in the passageway, but the presence of the diaphragm prevents the sensor from being contaminated by the fluid.

BRIEF DESCRIPTION OF THE DRAWINGS

FIG. 2 is an exploded view of the assembly of FIG. 1; and

FIG. 3 is an exploded view showing a sensor and a sensor port in accordance with certain embodiments.

DETAILED DESCRIPTION OF THE INVENTION

Figure 1:
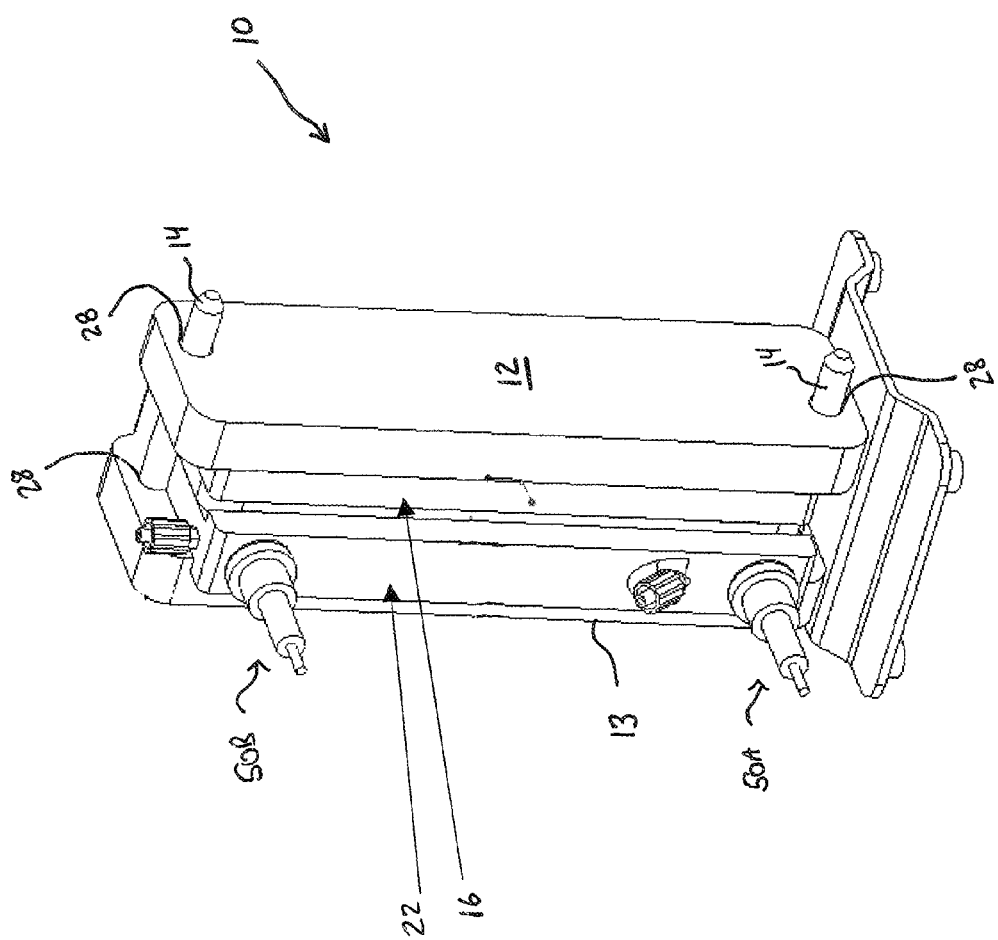
FIG. 1 is perspective view of a tangential flow filtration assembly in accordance with certain embodiments.

Turning first to FIG. 1, there is shown a filtration device 10 in accordance with certain embodiments. The device 10 includes a top holder plate 12 and a spaced bottom holder plate 13. The holder plates 12, 13 are preferably made of stainless steel and are sufficiently rigid and durable to provide accurate and effective mechanical constraint of the assembly against internal hydraulic operating pressures, such as 50-60 psi. Apertures 28 are provided in the holder plates 12, 13 and in each layer of the assembly to accommodate tie rods or threaded pins or bolts 14 or other clamping device to secure the assembly together. Spacers (not shown) can be provided, and can be spring-loaded. No filtration stream passageways are present in the holder plates 12, 13.

Positioned beneath holder plate 12 in the assembled state is disposable liner 16. The liner 16 is preferably made of inexpensive material, suitable for the application, that is acceptable for the particular assay, such as pharmaceutical assays, (and preferably is government approved). Suitable materials of construction include plastics, such as polystyrene, preferably polyolefins, such as polypropylene, polyethylene, copolymers and mixtures thereof. Polysulfone is particularly preferred in view of its strength and rigidity. The liner 16 is preferably molded with passageways and openings. Alternatively, and less preferred, it may be formed by milling, drilling and other such methods.

A filtration element 20 is sandwiched between liner 16 and a second disposable liner 22. The filtration element 20 can be a single membrane, and is preferably a plurality of stacked membranes, such as stacked ultrafiltration or microfiltration membranes, most preferably provided in the form of a cassette. Although a single cassette of membranes is shown, those skilled in the art will appreciate that multiple cassettes can be used. Suitable cassettes are sold under the name PELLICON® and are commercially available from Millipore Corporation.

As is conventional in the art, the liner 22 includes a first port 17A, one or more sub-ports 17C, a second port 17B and one or more sub-ports 17D (FIG. 2). Port 17A is for introduction of feed or removal of retentate, depending on its orientation within the assembly, with port 17B for removal of permeate, while preventing admixture of the filtrate with the retentate or feed, as is conventional. Port 17A is in fluid communication with the one or more sub-ports 17C. Port 17A is in fluid communication with 17C and with the sensor port closest to it. Port 17A also is in fluid communication with the feed port of the cassette, e.g., a PELLICON® cassette. Port 17B is in fluid communication with the one or more sub-ports 17D. Port 17B is only in communication with 17D and the permeate drain port of the cassette. The ports 17A and 17B may be located on opposite sides of the liner in order to provide adequate spacing and avoid interferences with other components. However, where spacing is sufficient or no interference occurs, they may be located on the same side. Each port 17A, 17B is in fluid communication with flow paths or passageways in the liner body that communicate with respective apertures to accommodate flow of feed, retentate or permeate as is conventional, thereby defining multiple flow paths for the filtration stream within the device.

The passageways can be tapered, narrowing as they proceed away from their respective port, to normalize pressure at each of the sub-ports 17C and 17D.

In certain embodiments, one side of one or both of the liners 16, 22 can include a plurality of inter-engaging ribs. The ribs provide added rigidity to the liners, and can be formed in the molding process. The ribs, when present, are positioned on the side of the liner that contacts the holder plate 12 or 13. The ribs extend from one side of the liner to the other, except where interrupted by a port. When assembled, there is significant clamping force applied to the filter element 20 and the liner, with sealing taking place between the smooth side of the liner 16, 22 and the filter element 20. The ribs assist in effectively assemble the liners in the filtration device of the invention, in sealing engagement upon the application of pressure, without the necessity of having corresponding grooves in the holder plates to mate with the ribs. Accordingly, the respective surfaces of the holder plates that abut the grids of the liners can be flat, and need not be specially designed to fit the liners.

In certain embodiments, one or more sensors, preferably two sensors such as feed pressure sensor 50A and retentate pressure sensor 50B, are removably connected to mount ports in one or more of the disposable liners. For purposes of illustration, two ports 30A, 30B are shown in liner 22. The port or ports 30A, 30B are each positioned to communication with a fluid path, so that a characteristic of the fluid in the fluid path (e.g., pressure) can be measured. A membrane or diaphragm 40, such as a diaphragm made of PVDF or polyolefin, preferably polyethylene, for example, is positioned over the port 30A (or 30B) in order to isolate, during operation, fluid in the fluid path from the sensor components. An O-ring 41 or the like can be used to seal the diaphragm 40 to the port. The membrane or diaphragm can be permanently attached to the port if desired.

In certain embodiments, the sensors are attached to the liner 22 using a diaphragm compression nut 52, as best seen in FIGS. 2 and 3. The nut 52 is internally threaded, the internal threads corresponding to external threads on a sensor compression nut 51 positioned on the sensor 50A so that the sensor 50A may be screwed into the nut 52. The sensor compression nut 51 compresses the sensor flange into the larger diaphragm compression nut 52. The nut 52 is also externally threaded, the external threads corresponding to threads in the port 30B so that the nut 52 may be screwed into the port. A slip washer 53 can be positioned between the compression nut 52 and the diaphragm as shown. The nut 52 compresses the O-ring 41, diaphragm 40 and washer 53 in place. Those skilled in the art will appreciate that other means of attaching the sensor to the mount port can be used, such as a press fit into the port or a suitable receptacle affixed to the port, clamps or fasteners that hold the sensor in place, etc.

In the assembled condition, the operative portion of the sensor is positioned directly against the membrane or diaphragm. The membrane or diaphragm is made of a sufficiently flexible material so that it deflects in response to pressure, remains continuous and does not break or lose the ability to isolate the sensor from the fluid path. The membrane or diaphragm can be semi-permeable or non-permeable. It is preferably of sterilizing grade.

The presence of two sensors 50A, 50B, one measuring feed pressure and the other retentate pressure, allows the transmembrane pressure to be calculated, as transmembrane pressure is the average of the feed and retentate pressures less the filtrate pressure. The filtrate pressure can be determined in a conventional manner well known to those skilled in the art. In use, the removable sensors are preferably in electrical communication with a control unit, which can record the relevant process parameters, such as feed pressure, retentate pressure, transmembrane pressure, etc., and can control the parameters accordingly.

By removably connecting the sensors to the mount ports on the disposable liner(s) in accordance with the embodiments disclosed herein, the sensors remain isolated from the fluid paths and can be readily removed from the liners and reused, while the liners can be discarded after use. This results in quick and easy system set up.

The length of the ports 30A and B are such that preferably there is little or no deadleg between the diaphragm of the sensor port and the conduit in which the fluid to be sensed passes. This ensures that no fluid is lost or becomes stagnant.

Suitable sensors include electromechanical sensors, due to cost, accuracy, reliability and availability concerns. Electromechanical sensors include a strain gauge bonded to a thin metal diaphragm. Deformation of the diaphragm results in deformation of the strain gauge, sending a proportional electrical signal to the control unit. Those skilled in the art will appreciate that sensors that operate using different technologies also could be used.

What is claimed is:

1. Filtration apparatus, comprising:
    a top plate;
    a bottom plate spaced from said top plate;
    a filtration member positioned between said top plate and said bottom plate;
    at least one disposable liner positioned between said top plate and said filtration member, said liner having a fluid inlet, a fluid outlet, at least one fluid path within said liner, and a sensor port in fluid communication with said fluid path;
    a diaphragm sealed to said sensor port; and
    a sensor removably connected to said sensor port for sensing pressure in said at least one fluid path through said diaphragm without contacting fluid in said fluid path.

2. The filter assembly of claim 1, wherein said liner further comprises at least a second fluid path, a second sensor port, and a second diaphragm sealed to said second sensor port, said filter assembly further comprising a second sensor removably connected to said second sensor port for sensing pressure in said second fluid path through said second diaphragm without contacting fluid in said second fluid path.

3. the filtration apparatus of claim 1, wherein said diaphragm comprises PVDF or polyethylene.

4. the filtration apparatus of claim 1, wherein said diaphragm is semi-permeable.

5. A liner for a filtration apparatus and adapted to seal between a holder plate and a filter element, said liner comprising a flat face adapted to abut said filter element and an opposite face adapted to abut said holder plate, said liner having a fluid inlet, a fluid outlet, at least one fluid path within said liner, and a sensor port in fluid communication with said fluid path;
   a diaphragm sealed to said sensor port; and
   a sensor removably connected to said sensor port for sensing pressure in said at least one fluid path through said diaphragm without contacting fluid in said fluid path.

6. The liner of claim 5, further comprising at least a second fluid path, a second sensor port, a second diaphragm sealed to said second sensor port, and a second sensor removably connected to said second sensor port for sensing pressure in said second fluid path through said second diaphragm without contacting fluid in said second fluid path.

* * * * *

UNITED STATES PATENT AND TRADEMARK OFFICE
CERTIFICATE OF CORRECTION

| | | |
|---|---|---|
| PATENT NO. | : 8,454,822 B2 | Page 1 of 1 |
| APPLICATION NO. | : 12/784094 | |
| DATED | : June 4, 2013 | |
| INVENTOR(S) | : Morrissey et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 373 days.

Signed and Sealed this
Thirtieth Day of September, 2014

Michelle K. Lee
*Deputy Director of the United States Patent and Trademark Office*